US012623036B2

(12) United States Patent
Fabien

(10) Patent No.: US 12,623,036 B2
(45) Date of Patent: May 12, 2026

(54) DEVICE FOR DISPENSING A FLUID PRODUCT

(71) Applicant: APTAR FRANCE SAS, Le Neubourg (FR)

(72) Inventor: David Fabien, Saint Renan (FR)

(73) Assignee: APTAR FRANCE SAS, Le Neubourg (FR)

( * ) Notice: Subject to any disclaimer, the term of this patent is extended or adjusted under 35 U.S.C. 154(b) by 736 days.

(21) Appl. No.: 18/009,268

(22) PCT Filed: Jun. 8, 2021

(86) PCT No.: PCT/FR2021/051027
§ 371 (c)(1),
(2) Date: Dec. 8, 2022

(87) PCT Pub. No.: WO2021/250350
PCT Pub. Date: Dec. 16, 2021

(65) Prior Publication Data
US 2023/0256180 A1     Aug. 17, 2023

(30) Foreign Application Priority Data
Jun. 10, 2020    (FR) ...................................... 2006060

(51) Int. Cl.
*A61M 11/00*          (2006.01)
*A61M 15/00*          (2006.01)
(52) U.S. Cl.
CPC ...... *A61M 11/007* (2014.02); *A61M 15/0081* (2014.02); *A61M 15/0083* (2014.02); *A61M 2205/103* (2013.01)
(58) Field of Classification Search
CPC .... A61M 11/00–08; A61M 15/00–085; A61M 2205/103; A61M 2205/276
See application file for complete search history.

(56) References Cited

U.S. PATENT DOCUMENTS

2010/0084433 A1     4/2010  Cater et al.
2018/0060527 A1*    3/2018  Kalyanpur ............. G16H 40/63

FOREIGN PATENT DOCUMENTS

FR          3072294 A1     4/2019

OTHER PUBLICATIONS

International Search Report for PCT/FR2021/051027 dated Sep. 17, 2021.

(Continued)

*Primary Examiner* — Rachel T Sippel
*Assistant Examiner* — Jacqueline M Pinderski
(74) *Attorney, Agent, or Firm* — Sughrue Mion, PLLC

(57)                    ABSTRACT

A dispenser having a tank, a dispensing head having an axially moveable dispensing port, a dispensing member actuated when the tank is moved upwards, an inner body having a hollow cylinder receiving the dispenser and an axial extension extending downwards, a control module having an electronic board, a motor and a motor wheel, an outer body receiving the inner body and control module, a thrust member in contact with the tank and axially movable on the inner body between rest and actuation positions, a control member attached to the thrust member and axially moving therewith, and a locking ring mounted on the axial extension rotatable between locking and releasing positions. The locking ring is moved by the control module into the locking position with the thrust member to prevent axial movement of latter and into the releasing position with the thrust member to enable axial movement towards the actuation position.

18 Claims, 9 Drawing Sheets

(56)                    References Cited

OTHER PUBLICATIONS

International Preliminary Report on Patentability (with translation of Written Opinion) dated Dec. 13, 2022 in International Application No. PCT/FR2021/051027.

* cited by examiner

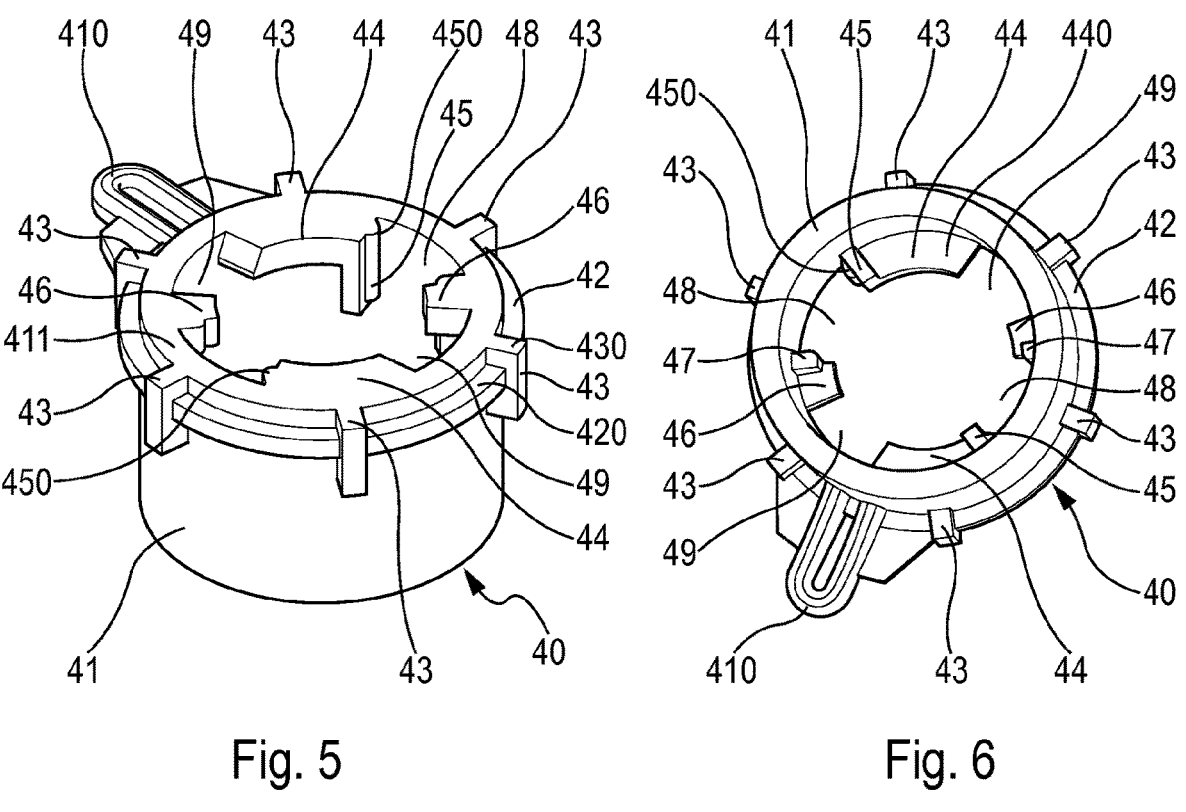
Fig. 5                    Fig. 6
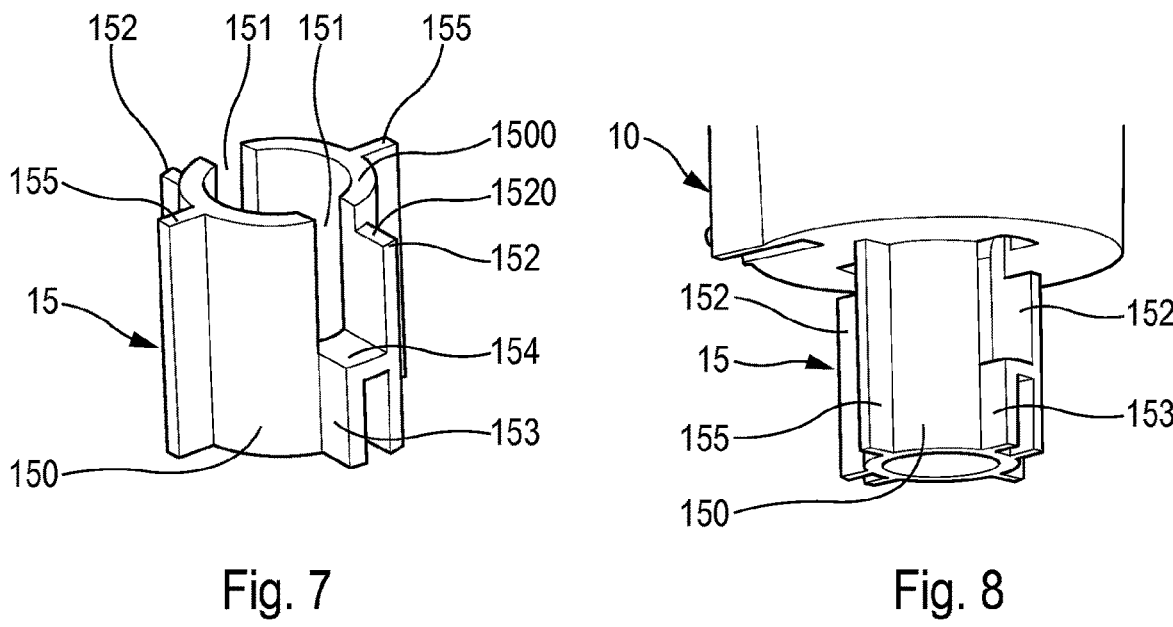
Fig. 7                    Fig. 8

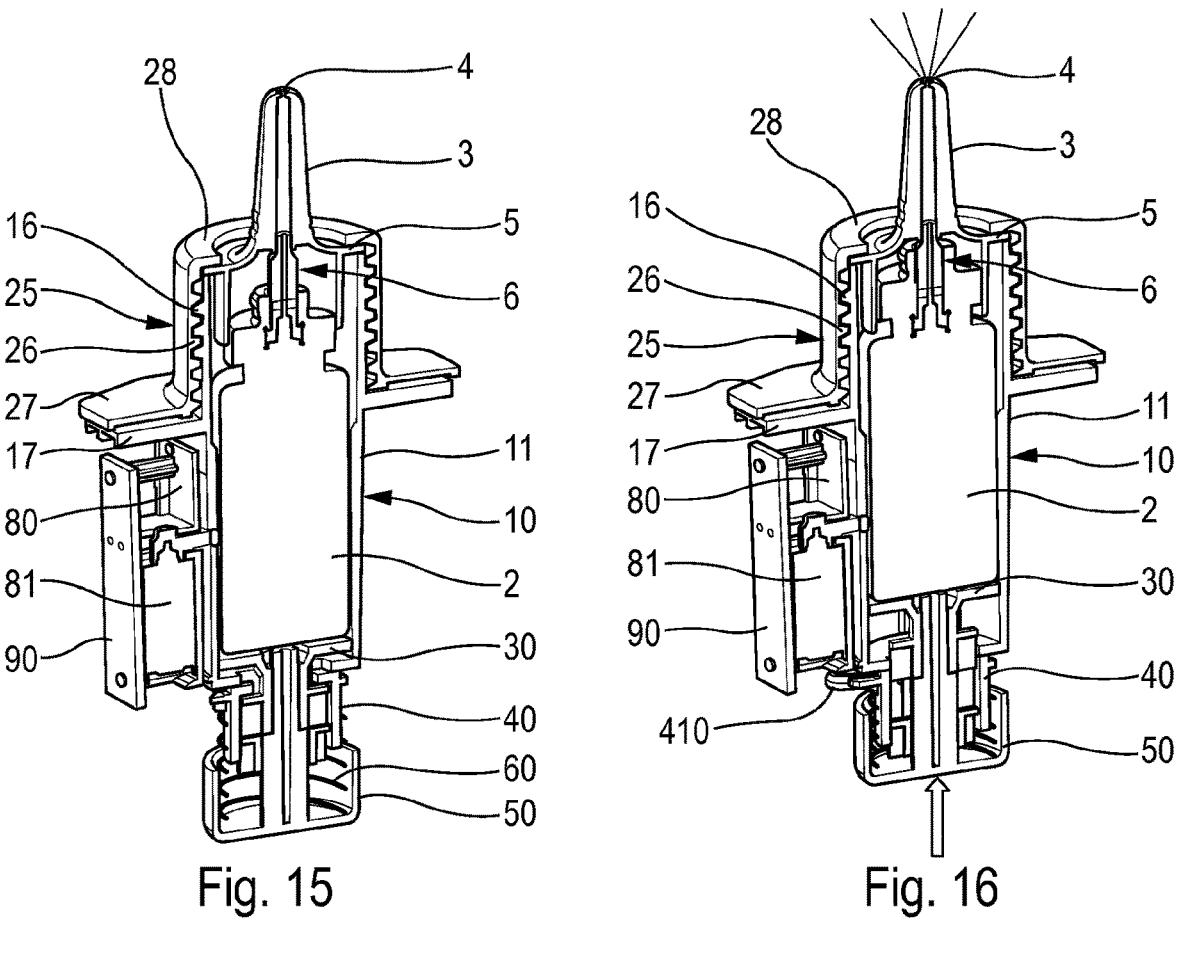
Fig. 15
Fig. 16
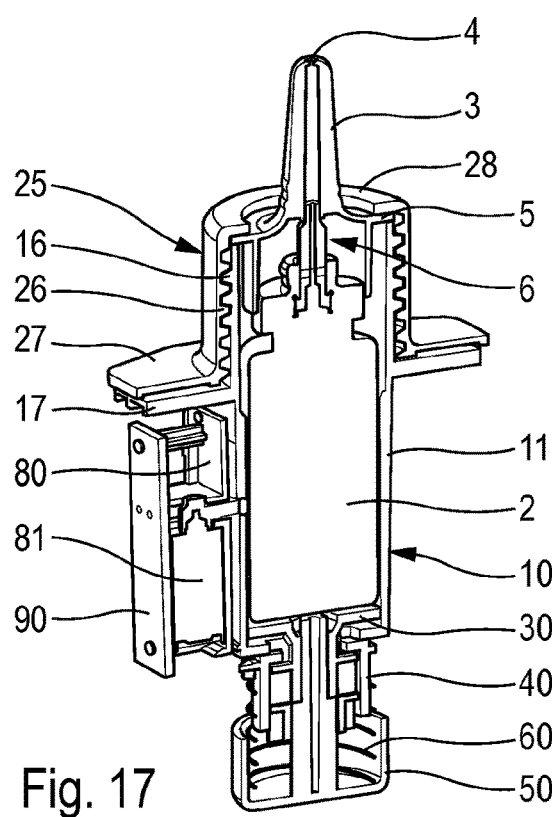
Fig. 17

DEVICE FOR DISPENSING A FLUID PRODUCT

This Application is a National Stage of International Application No. PCT/FR2021/051027 filed Jun. 8, 2021, claiming priority based on French Patent Application No. 2006060 filed Jun. 10, 2020.

The present invention relates to a device for dispensing a fluid product.

BACKGROUND OF THE INVNETION

1. Field of the Invention

Today, there are certain situations in which it may be necessary to administer certain fluid products, such as potent drugs which are potentially lethal to humans. This is particularly the case for the treatment of particular pathologies or for people who require palliative treatments in end-of-life contexts. Handling such substances requires extreme caution and extremely safe administration devices to avoid the risk of overdose, which may occur if several consecutive doses are administered together. Another risk relates to the use of these devices by any person other than the person for whom the treatment is intended, e.g., children.

Document FR3072294 describes a prior-art device.

Non-Limiting Objects of the Invention

The present invention aims to provide a device for dispensing a fluid product that does not have the above mentioned disadvantages.

In particular, the present invention aims to provide a device for dispensing a fluid product that is safe and secure for the user, especially to avoid the risk of overdose.

The present invention also aims to provide a device for dispensing a fluid product that can be used only by authorised persons, in particular by the person in therapeutic need.

The present invention also aims to provide a device for dispensing a fluid product that is blocked for a predetermined period of time between two successive actuations.

The present invention also aims to provide a device for dispensing a fluid product that allows the device to be actuated only for a predetermined period of time, and that, in the absence of actuation, automatically re-locks at the end of said period of time.

The present invention also aims to provide a device for dispensing a fluid product that is robust and reliable to use.

The present invention also aims to provide a device for dispensing a fluid product that is simple and inexpensive to manufacture and to assemble.

The present invention thus provides a device for dispensing a fluid product that comprises a:

- a fluid product dispenser having a tank containing a fluid product, a dispensing head having a dispensing port, said dispensing head being axially movable with respect to said tank, and a dispensing member, such as a pump or a valve, mounted on said tank, said dispensing member being actuated when said tank is moved axially upwards with respect to said dispensing head;
- an inner body comprising a hollow cylinder receiving said dispenser and an axial extension extending axially downwards from said hollow cylinder;
- a control module attached to said inner body, said control module comprising an electronic board, a motor and a motor wheel caused to rotate by said motor;

- an outer body receiving said inner body and said control module;
- a thrust member in contact with said tank and mounted so as to be axially movable on said inner body between a rest position and an actuation position;
- a control member attached to said thrust member and axially moving together therewith;
- a locking ring mounted on said axial extension of said inner body so as to be capable of rotating between locking and releasing positions, said locking ring being moved between the latter locking and releasing positions by said control module, said locking ring co-operating in the locking position with said thrust member so as to prevent axial movement of the latter and co-operating in the releasing position with said thrust member so as to enable axial movement of the latter towards the actuation position thereof.

Advantageously, said control module comprises a flexible element attached on one side to said inner body and on the other side to said locking ring, said motor wheel co-operating with said flexible element to deform it and thus move said locking ring between its locking and releasing positions.

Advantageously, said flexible element is a wire, or a flexible blade.

Advantageously, said axial extension of said inner body comprises a hollow axial cylinder provided with at least one axial slot extending over a portion of its height, said hollow axial cylinder comprising at least one radial wall extending radially outwards over the entire height of said hollow axial cylinder, said at least one radial wall being angularly offset from each axial slot by 90°.

Advantageously, said hollow axial cylinder comprises two diametrically opposite slots and two diametrically opposed radial walls.

Advantageously, said thrust member comprises an axial well extending axially downwards from an upper plate co-operating with said tank, said axial well comprising at least one radial extension extending radially outwards from the outer surface of said axial well, the upper axial surface of each radial extension being arranged away from said upper plate, each radial extension being arranged in a respective axial slot of said inner body.

Advantageously, said thrust member comprises two diametrically opposed radial extensions.

Advantageously, said upper plate of said thrust member comprises, at an outer edge, a radial projection for attaching a slider co-operating during actuation with said control module.

Advantageously, said locking ring comprises a hollow sleeve provided with at least one first flat inner surface extending radially inwards from an upper axial edge of said hollow sleeve, each first flat inner surface extending over a small part of the inner periphery of said hollow sleeve, said upper axial surface of a radial extension of said thrust member being in axial abutment against a respective first flat inner surface when the locking ring is in the locking position.

Advantageously, in the releasing position of said locking ring, said at least one first flat inner surface is angularly offset from said respective radial extension, thus allowing axial movement of said thrust member relative to said inner body.

Advantageously, said at least one radial wall co-operates with said locking ring to define its locking and releasing positions.

Advantageously, said locking ring is blocked in the releasing position throughout the actuation cycle, and returns automatically to the locking position at the end of actuation.

Advantageously, said control module deforms said flexible element from the start of the axial movement of the control member, so as to force said locking ring to the locking position.

Advantageously, said control module comprises time-out means to prevent, after each actuation of the dispenser, movement of said locking ring from the locking position to the releasing position for a predetermined period of time.

Advantageously, said time-out means block a control button of the device and/or said motor.

Advantageously, said fluid product is a pharmaceutical product, such as a drug.

These characteristics and advantages and others of the present invention appear more clearly from the following detailed description, given by way of non-limiting example, and with reference to the accompanying drawings, and in which:

BRIEF DESCRIPTION OF THE DRAWINGS

FIG. 5 is a diagrammatic perspective view as seen from above of the locking ring, according to an advantageous embodiment;

FIG. 6 is a diagrammatic perspective view as seen from below of the locking ring in FIG. 5;

FIG. 7 is a diagrammatic and fragmentary perspective side view of the axial extension of the inner body, according to an advantageous embodiment;

FIG. 8 is a diagrammatic and fragmentary perspective side view of the axial extension of the inner body;

FIGS. 15 to 17 are cut-away diagrammatic perspective views showing an actuation cycle of the dispenser arranged in the device, respectively before, during and after a dose of fluid is dispensed;

DETAILED DESCRIPTION OF THE INVENTION

Figure 1:
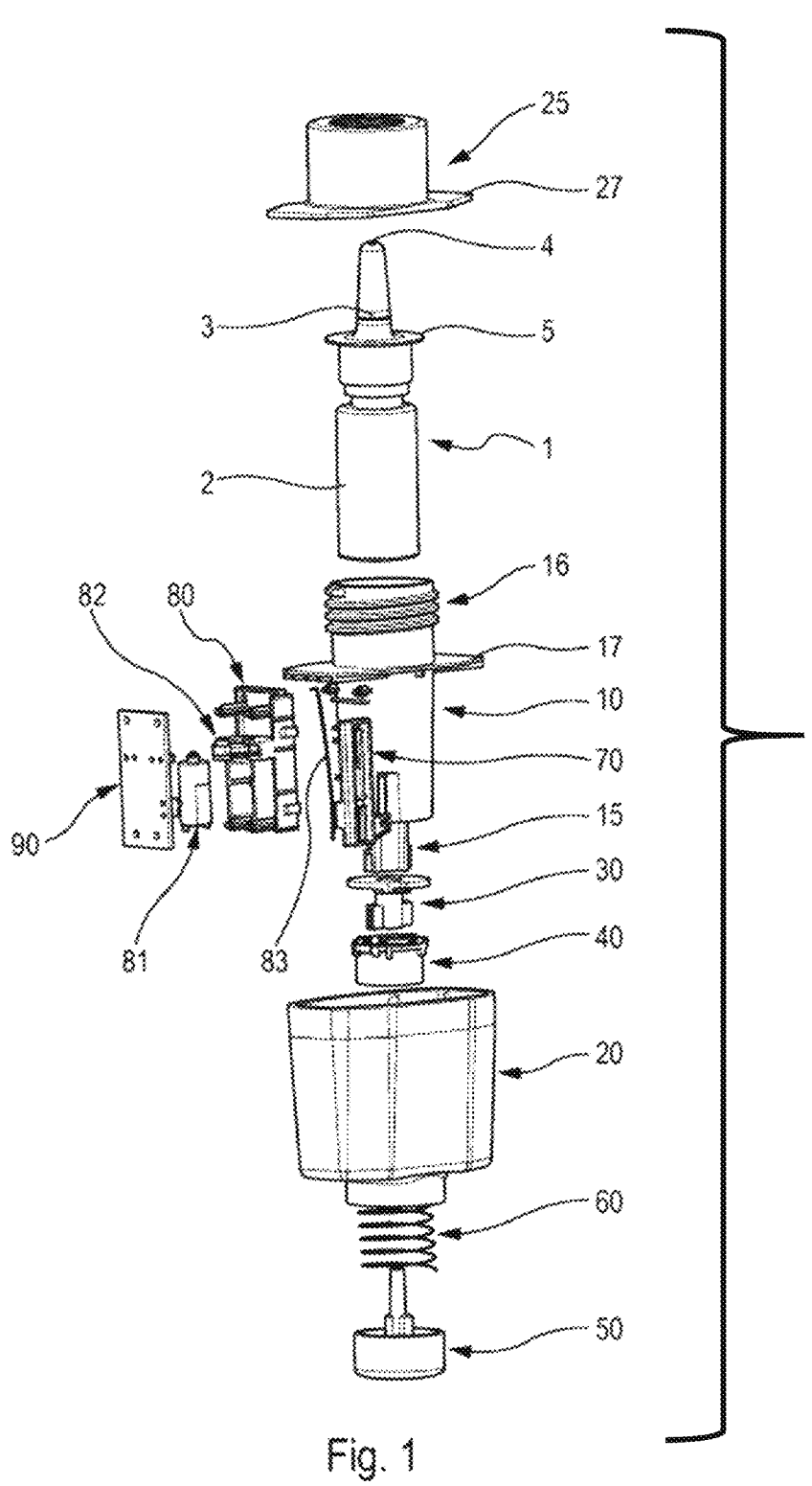
FIG. 1 is an exploded diagrammatic perspective view of a dispensing device according to an advantageous embodiment.

The terms "axial" and "radial" are relative to the longitudinal central axis of the device. The terms "top", "bottom", "upper" and "lower" refer to the upright position of the device represented in FIG. 2.

The main object of the present invention is a device that authorises/prohibits the delivery of a dose by blocking/releasing the actuation of an actuating member allowing the actuation of a fluid product dispenser.

The device for dispensing a fluid product shown in the figures comprises a fluid product dispenser 1, advantageously of the standard type. The fluid is preferably a pharmaceutical product, such as a drug. The dispenser 1 comprises a tank 2 containing the fluid product and a dispensing head 3 that is axially movable with respect to the tank 2. The dispensing head 3 is provided with a dispensing port 4 and a radial bearing surface 5 that makes it possible in particular to manually actuate said dispenser. A dispensing member 6, such as a pump or a valve, is mounted onto the tank 2, said dispensing member being actuated when the tank 2 is moved axially upwards with respect to the dispensing head 3. Generally, when the tank 2 does not contain propellant gas, a metering pump is used, and when the tank 2 contains propellant gas, a metering valve is used. These two types of dispensing member are well known to the person skilled in the art, and since this dispensing member does not intervene directly in the present invention, it will not be described in any further detail below.

The device for dispensing a fluid product also comprises an inner body 10, receiving the dispenser 1, and an outer body 20, receiving the inner body 10.

The inner body 10 comprises a hollow cylinder 11 that is axially open on the upper side, with coupling means which are advantageously made in the form of a thread 16 on the outer surface of the upper opening. A radial flange 17 radially extends outwards below said thread 16. On the lower side, the inner body 10 comprises an axial extension 15, extending axially downwards from said hollow cylinder 11. This axial extension 15, as can be seen in FIGS. 7 and 8, has a smaller radial dimension than the diameter of said hollow cylinder 11. It may be moulded integrally with the inner body 10, or it may be manufactured separately and then attached to said inner body 10 in any appropriate manner. The axial extension 15 comprises a hollow axial cylinder 150 provided with at least one axial slot 151 extending over a portion of its height. In the embodiment shown in the drawings, two diametrically opposed axial slots 151 are present. Each axial slot 151 comprises a first lateral fin 152 extending outwards from a lateral edge of said axial slot 151. Advantageously, this first lateral fin 152 comprises an upper axial edge 1520 offset axially downwards with respect to the upper axial edge 1500 of the hollow axial cylinder 150. The advantage of this configuration is described below. Below each axial slot 151, there is a second lateral fin 153 that extends parallel to said first lateral fin 152, said first and second lateral fins 152, 153 being connected by a flat surface 154 that forms the bottom of each axial slot 151 and extends it radially outwards. The hollow axial cylinder 150 comprises at least one radial wall 155 extending radially outwards over the entire height of said hollow axial cylinder, said at least one radial wall 155 being angularly offset from each axial slot by 90°. In the embodiment shown in the drawings, two diametrically opposed radial walls 155 are present.

The outer body 20 is hollow and may have any outer shape. In the embodiment shown, the outer body 20 is octagonal in shape that corresponds to the shape of said radial flange 17 of the inner body 10. The outer body 20 is attached in an appropriate manner to the inner body 10, e.g., by snap-fastening. Advantageously, the outer body 20 comprises, on the outside, one or a plurality of display units 21, e.g., a screen, making it possible to display information, e.g., instructions for use, battery charging information, etc. The display 21 may also incorporate an actuation zone, e.g., a tactile control button, which the user presses to unlock the device. In a variant, a control button that is separate from the display unit 21 may also be provided. Advantageously, the control button or zone may incorporate fingerprint detection means to allow the device to be actuated only by the authorised person or persons, and thus prevent any accidental actuation, for example by children. Other means of recognition may be envisaged, such as facial recognition.

A cover 25 is provided for attaching the dispenser 1 to the unit that is formed by the inner body 1 and outer body 20. This cap 25 comprises a hollow cylinder open axially on both sides, with complementary coupling means, advantageously made in the form of an inner thread 26, adapted to co-operate with the coupling means of the inner body 10. A first radial flange 27 is provided at the lower opening, having a shape corresponding to the radial flange 17 of the inner body 10, and to the outer shape of the outer body 20. A second radial flange 28 is provided at the upper opening, to wedge the bearing surface 5 of the dispenser 1 between the upper axial edge of the inner body 10 and said second radial flange 28 of the cap 25.

Figures 2, 3, 4:
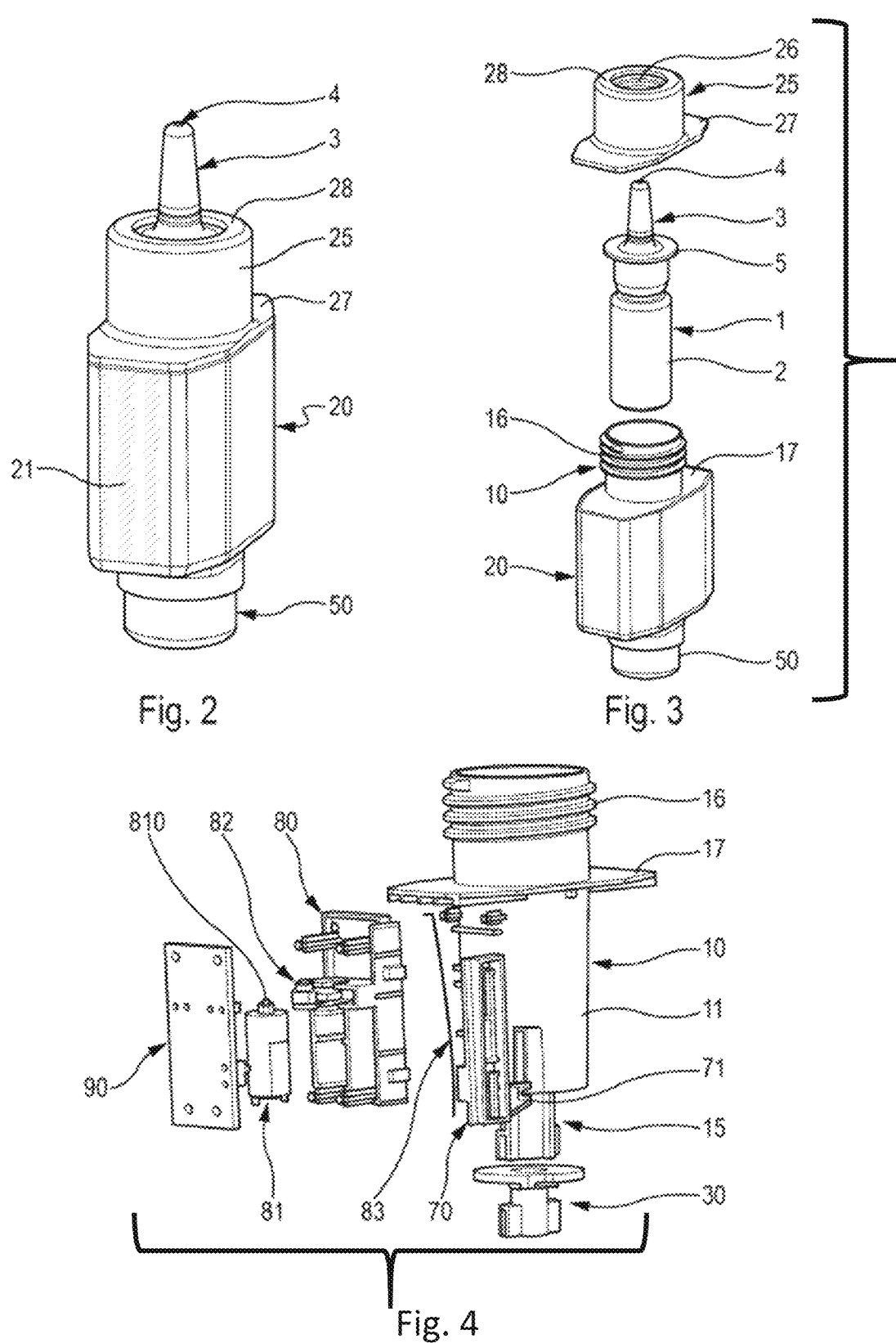
FIG. 2 is a diagrammatic perspective side view of the device in FIG. 1 after assembly.
FIG. 3 is an exploded diagrammatic perspective view illustrating the assembly of the fluid product dispenser within the device.
FIG. 4 is an exploded diagrammatic and fragmentary perspective view of an inner portion of the device in FIG. 1.

Thus, to assemble the dispenser 1 in the device, the tank 2 is inserted inside the hollow cylinder 11 of the inner body 10, until the radial bearing surface 5 of the dispensing head 3 comes to rest on the upper axial edge of the inner body 10. The cap 25 is then screwed onto said inner body 10, and in the assembled position of the cap 25, the first radial flange 27 of the cap 25 covers the radial flange 17 of the inner body 10 and closes the upper opening of the outer body 20. This assembled position is shown in FIG. 2.

The action of wedging the radial bearing surface of dispenser 1 is advantageous in limiting the axial clearance of the dispenser in the device, liable to generate malfunctions.

The device further comprises a thrust member 30, a locking ring 40, an actuator 50, and a spring 60 for said actuator.

The thrust member 30 and the actuator 50 are attached to each other, both axially and in rotation, and move together axially with respect to the inner body 10 between a rest position and an actuation position. Advantageously, the thrust member 30 is first inserted into the inner body 10 from above, thus being arranged in said inner body 10 directly under the tank 2. In this case, the thrust member 30 is attached to the actuator 50 at the time of the final assembly of the device, after the locking ring 40 has been interposed between them, for example by crimping of the hot stamping type. Other attachments may also be envisaged.

Figures 9, 10, 11, 12, 13, 14:
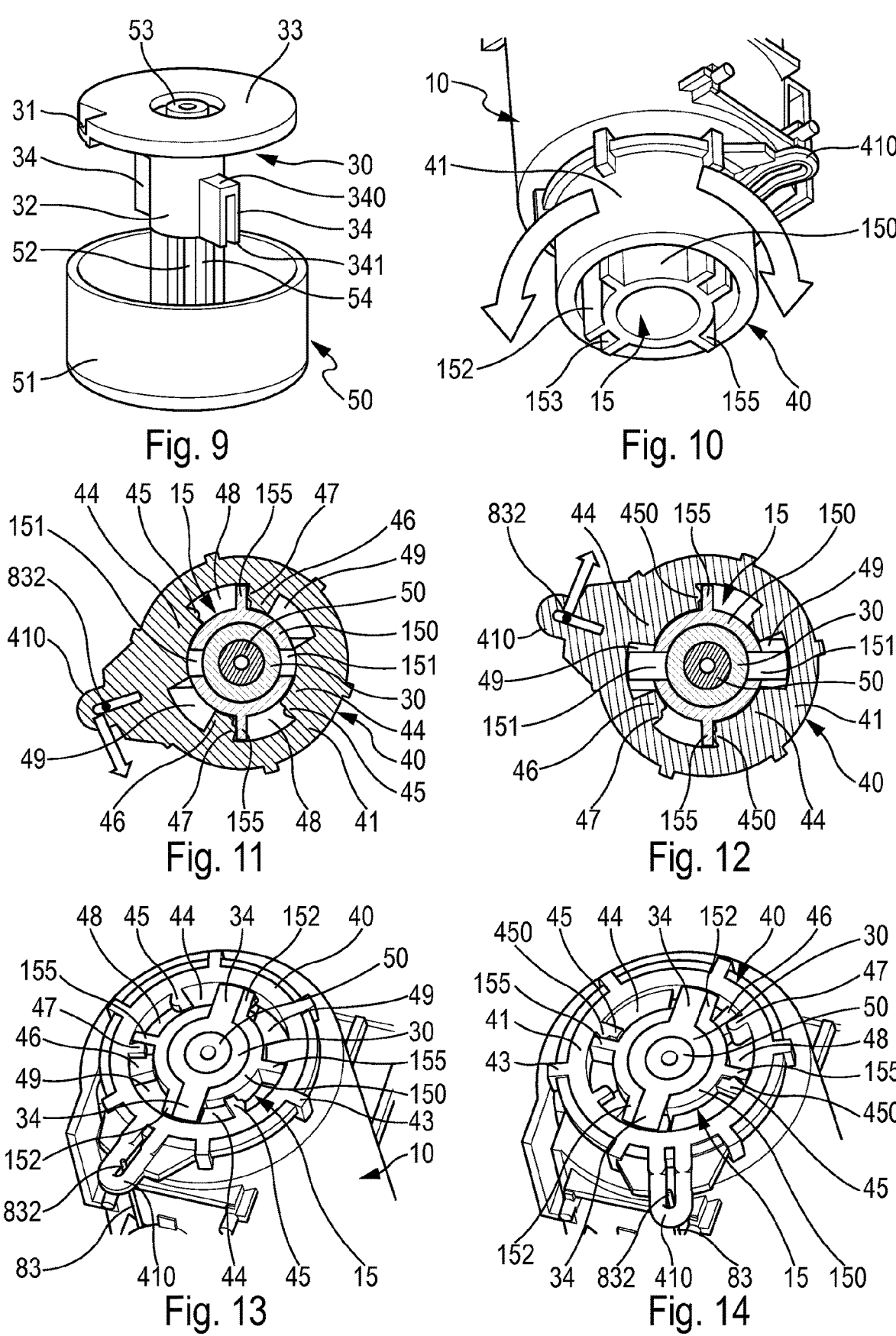
FIG. 9 is a diagrammatic perspective side view of the thrust member attached to the control member, according to an advantageous embodiment.
FIG. 10 is a diagrammatic and fragmentary perspective view from below of the locking ring assembled around the axial extension of the inner body.
FIG. 11 is a diagrammatic cross-sectional view showing the locking ring in the locking position.
FIG. 12 is a diagrammatic cross-sectional view showing the locking ring in the releasing position.
FIG. 13 is a cut-away diagrammatic and fragmentary perspective view as seen from above of the locking ring in the locking position.
FIG. 14 is a cut-away diagrammatic and fragmentary perspective view as seen from above of the locking ring in the releasing position.

The thrust member 30, shown in FIG. 9, comprises a radial projection 31, having a function that is described below. It also comprises an axial well 32 extending axially downwards from an upper plate 33. The radial projection 31 is provided advantageously at an outer edge of the upper plate 33. The axial well 32 comprises at least one radial extension 34 extending radially outwards from the outer surface of said cylindrical axial well 32. The upper axial surface 340 of each radial extension 34 is arranged away from said upper plate 33. In the embodiment shown in the figures, two diametrically opposed radial extensions 34 are present. Each radial extension 34 is arranged in a respective axial slot 151 of the inner body 10. In the rest position, the lower axial edge 341 of each radial extension 34 rests on a respective flat surface 154 of the inner body, blocking said thrust member 30 against any downward axial movement with respect to the inner body 10, as can be seen in particular in FIG. 18. In the actuation position, each radial extension 34 has moved upwards in its respective axial slot 151, as can be seen in particular in FIG. 20.

The actuator 50 comprises a blind cylinder 51, the bottom of which forms the bearing surface for the user. A central rod 52 extends axially upwards and is adapted to pass through the axial well 32 of the thrust member 30. The upper end 53 of the central rod 52 makes it possible to fix the thrust member 30 to the actuator 50. Radial profiles 54, such as ribs, can be provided on a lower part of said axial rod 52, to define the abutment position of the thrust member 30 with respect to the actuator 50.

The locking ring 40 is mounted to rotate about said axial extension 15 of the inner body 10 between a locking position and a releasing position. It co-operates with said axial extension 15 and with said thrust member 30 to selectively block or allow said thrust member 30 to move axially together with said actuator 50. The locking ring 40 comprises a hollow sleeve 41 provided at an upper axial edge 411 of a control part 410 extending radially outwards. As can be seen in particular in FIGS. 5 and 6, the control part 410 may form an eyelet, but other shapes are possible. In the proximity of its top axial edge 411, the hollow sleeve 41 comprises a radial ring 42 that extends radially outwards around said hollow sleeve 41. The upper axial edge 420 of said radial ring 42 is offset axially downwards with respect to the upper axial edge 411 of the hollow sleeve 41. A plurality of radial projections 43 are arranged around said radial ring 42, extending axially as far as the upper axial edge 411 of the hollow sleeve 41 and radially outwards beyond said radial ring 42. Said radial projections 43 extend axially downwards beyond the lower axial edge of said radial ring 42. In the embodiment shown in the drawings, there are six radial projections 43 distributed over the periphery of said radial ring 42 being advantageously angularly equidistant by 60°. The locking ring 40 comprises at least one first flat inner surface 44 extending radially inwards from the upper axial edge 411 of the hollow sleeve 41. In the embodiment shown in the drawings, two diametrically opposed first flat inner surfaces 44 are present. Each first flat inner surface 44 extends over a small portion of the inner periphery of said hollow sleeve 41 and comprises, on one side, a first axial upright 45 extending axially downwards from the upper axial edge 411 of the hollow sleeve 41, over a portion of the height of said hollow sleeve 41. This first axial upright 45 also extends radially inwards, like the flat inner surface 44. The lateral side of the first axial upright 45 turned away from the flat inner surface 44 advantageously comprises a projecting profile 450, such as a rounded bead, visible more particularly in FIG. 5. The lower axial surface 440 of each first flat inner surface 44 co-operates in the locking position with a radial extension 34 of the thrust member 30 to prevent said thrust member 30 from moving axially.

Advantageously, in the locking position, each first flat inner surface 44 also extends above the upper axial edge 1520 of a respective first lateral fin 152, which guarantees better resistance to the force of the user by preventing the locking ring 40 from overhanging.

However, it should be noted that such a configuration is not essential. The locking ring 40 comprises also at least one second flat inner surface 46 extending radially inwards from the upper axial edge 411 of the hollow sleeve 41. In the embodiment shown in the drawings, there are two diametrically opposed second flat inner surfaces 44, offset by 90° with respect to the first flat inner surfaces 44. Each second flat inner surface 46 extends over a small portion of the inner periphery of said hollow sleeve 41 and comprises, on one side, a second axial upright 47 extending axially downwards from the upper axial edge 411 of the hollow sleeve 41, over a portion of the height of said hollow sleeve 41. This second axial upright 47 also extends radially inwards, but less so than the second flat inner surface 46, as can be seen in FIG. 6. Each second axial upright 47 faces the adjacent first axial upright 45, defining a first angular space 48 between them.

Figures 20, 21:
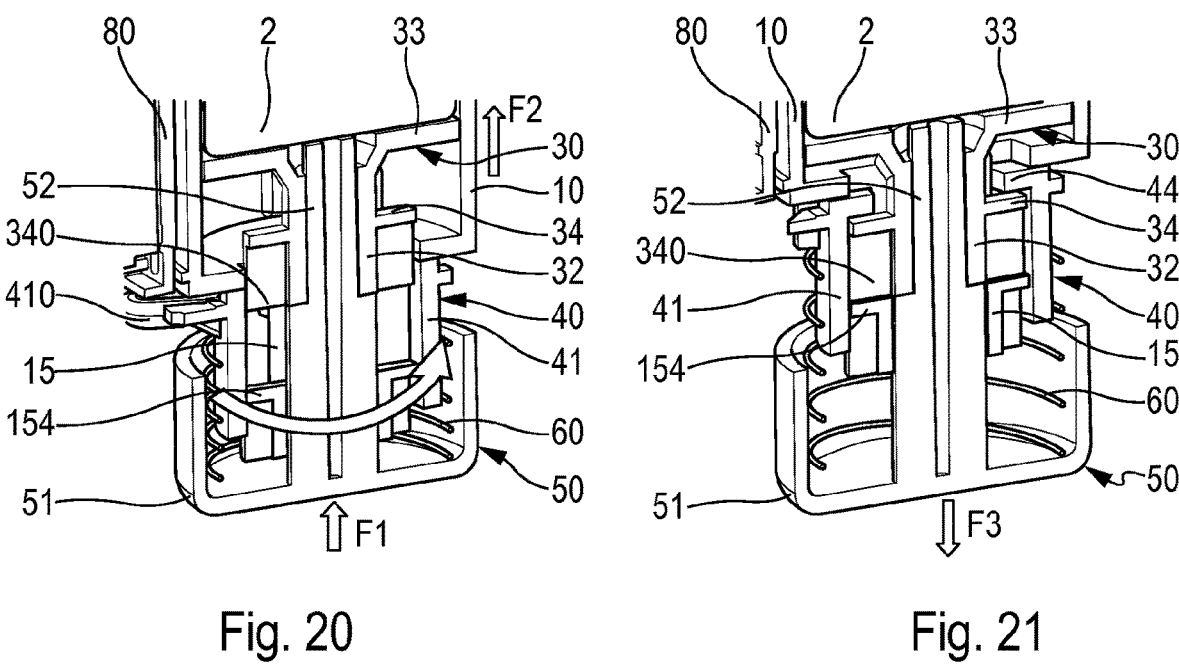
FIG. 20 is a view similar to the view in FIG. 19, the thrust and control members being in the actuation position.
FIG. 21 is a view similar to the view in FIG. 20, after actuation, the locking ring being returned to the locking position and the thrust and control members being returned to the rest position.
Figures 29, 30:
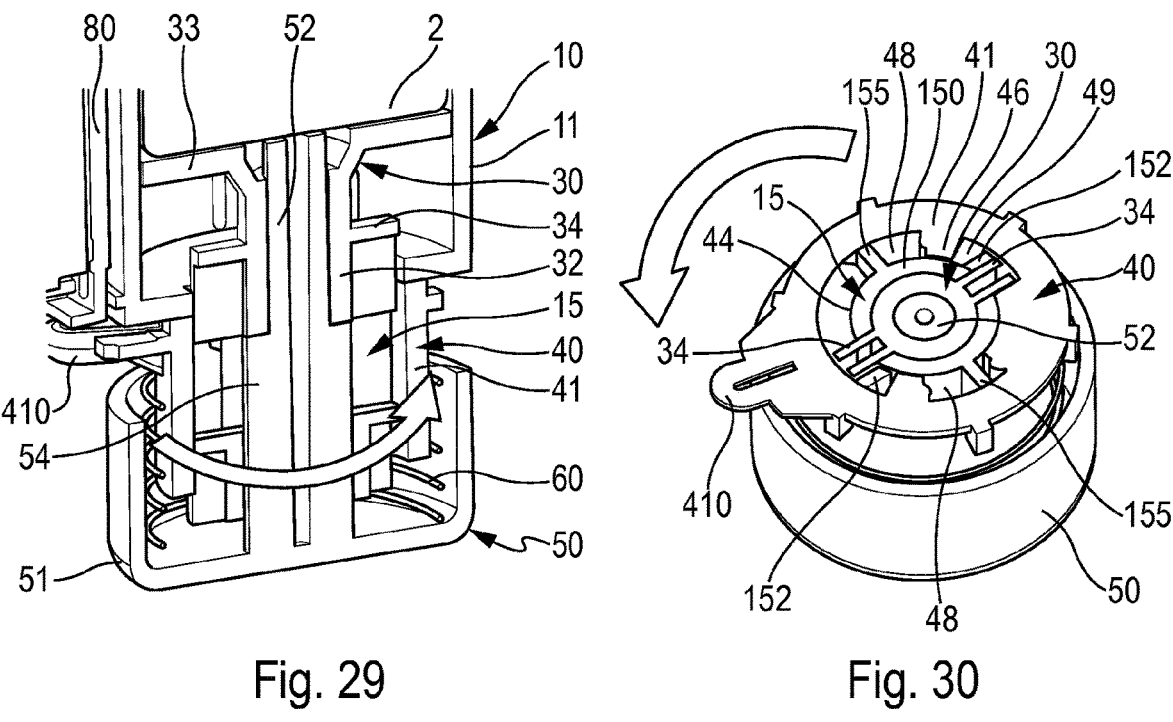
FIG. 29 is a view similar to the view in FIG. 20.
FIG. 30 is a cut-away diagrammatic and fragmentary perspective view as seen from above of the locking ring blocked in the releasing position by the thrust member during actuation of the device.
Figures 31, 32, 33:
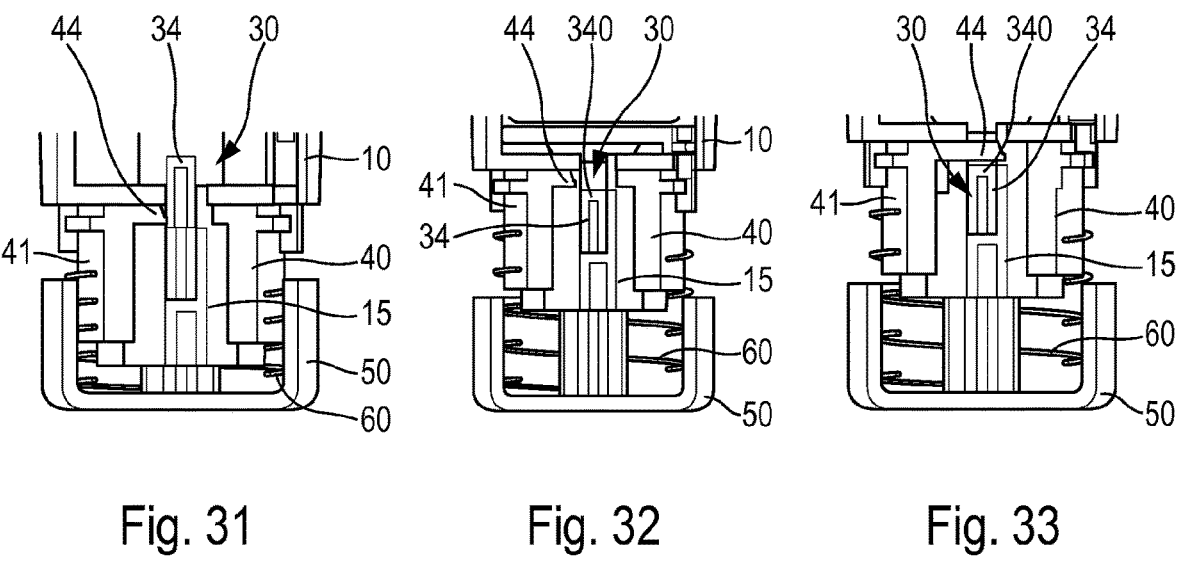
FIG. 31 is a cut-away diagrammatic and fragmentary perspective side view showing the locking ring blocked in the releasing position by the thrust member in the actuation position.
FIG. 32 is a view similar to the view in FIG. 31, showing the thrust member returned to the rest position, and thus no longer blocking the locking ring.
FIG. 33 is a view similar to the view in FIG. 32, showing the locking ring returned to the locking position.

Similarly, on the other side, a second angular space 49 is defined between the first and second plane inner surfaces 44, 46. In the embodiment shown, there are therefore two first angular spaces 48 which are diametrically opposed, and two second angular spaces 48 which are diametrically opposed. Each first angular space 48 receives a radial wall 155 of the axial extension 15 of the inner body 10. The turning amplitude of the locking ring 40 is therefore defined by this first angular space 48. The locking ring 40 is in the locking position when each radial wall 155 abuts against a second axial upright 47, as can be seen in FIGS. 11 and 13. In this locking position, the upper axial surface 340 of each radial extension 34 of the thrust member 30 rests against the lower axial surface 440 of a respective flat inner surface 44, thereby preventing the upward axial movement of the thrust member 30 and therefore of the tank 2. The locking ring 40 is in the releasing position when each radial wall 155 abuts against a first axial upright 45, as can be seen in FIGS. 12 and 14. In this releasing position, each flat inner surface 44 has rotated with respect to the respective radial extension 34, such that each radial extension 34 faces a second angular space 49, which allows the upward axial movement of the thrust member and therefore of the tank 2. From the start of the axial movement and up to the actuation position of the thrust member 30, each radial extension 34 extends in a respective second angular space 49, which blocks the locking ring 40 in rotation in the releasing position, as can be seen in FIGS. 20, 30 and 31. The locking ring 40 can thus return to the locking position only when the thrust member 30 and control member 50 have returned to the rest position.

The spring 60 returns the actuator 50 and the thrust member 30 to the rest position at the end of actuation, when the user releases the actuating force on the actuator 50. Advantageously, it is arranged between the bottom of the blind cylinder 51 of the actuator 50 and a portion of the locking ring 40, advantageously the lower axial edge of the radial projections 43.

Figures 34, 35, 36:
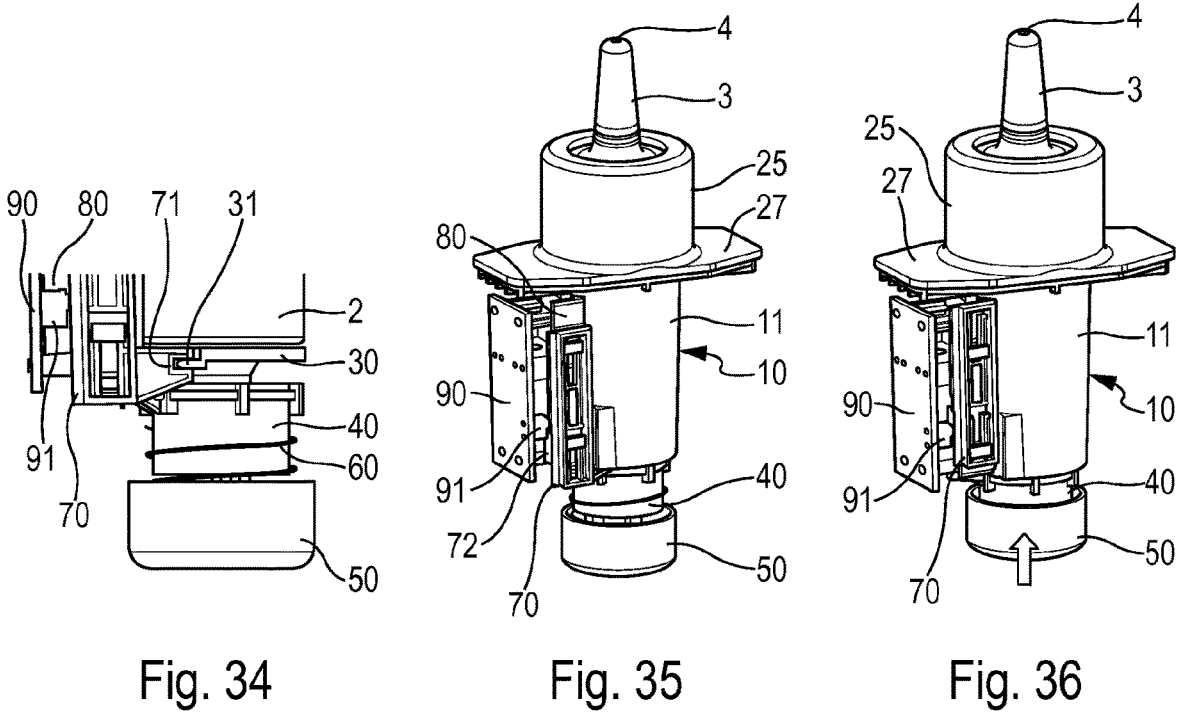
FIG. 34 is a diagrammatic and fragmentary perspective side view showing the slider attached to the thrust member.
FIGS. 35 and 36 are diagrammatic and fragmentary perspective views showing the slider respectively before actuation and after the start of its axial movement during actuation.

A slider 70 is mounted in stationary manner on the thrust member 30, and is therefore axially movable together with it, being arranged outside the inner body 10. Advantageously, the slider 70 comprises a profile 71, such as a radial groove, adapted to be attached to the radial projection 31 of the thrust member 30, as can be seen in FIG. 34. The slider 70 comprises also a projecting contact surface 72 having a function that is described below.

A control module is attached to the outside of said inner body 10 and received inside said outer body 20. This control module comprises a support body 80, attached to the inner body 10, on which are assembled a motor 81, a motor wheel 82, a flexible element 83 and an electronic board 90.

The motor 81 may be a 3V direct current gear motor adapted to rotate a motor shaft 810 in two opposite directions. This motor may be powered in any appropriate manner, e.g., by means of rechargeable or non-rechargeable batteries or accumulators.

Figures 22, 23, 24, 25:
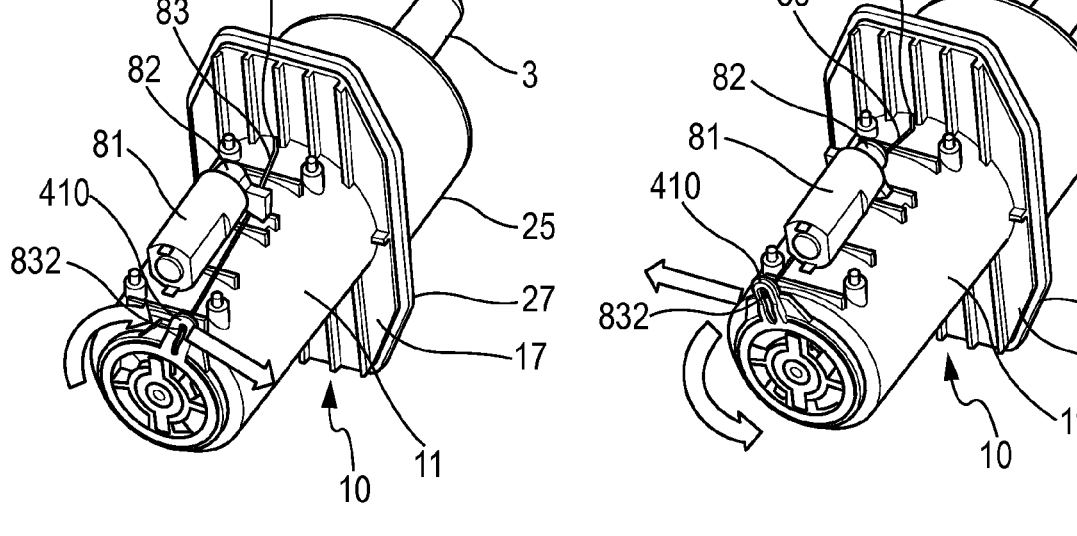
FIG. 22 is a diagrammatic and fragmentary perspective view showing the electronic board, motor wheel and slider.
FIG. 23 is a diagrammatic and fragmentary perspective side view showing the flexible element co-operating with the inner body, motor wheel and locking ring.
FIG. 24 is a view similar to the view in FIG. 23, showing the locking ring moved to the locking position by the flexible element that is deformed in a first direction by the motor wheel.
FIG. 25 is a view similar to the view in FIG. 24, showing the locking ring moved to the releasing position by the flexible element that is deformed in the opposite direction by the motor wheel.

The motor wheel 82 is mounted on the motor shaft 810, and is therefore caused to rotate in one or the other direction, according to the instructions transmitted to the motor by the control module. This motor wheel 82, as can be seen in FIGS. 22 and 23, comprises an axle 820 which receives the motor shaft 810, and a recess 821, defined between two teeth 822, 823, said recess receiving the flexible element 83 to move it in one direction or the other.

The flexible element 83 is advantageously a wire or blade that can be elastically deformed, comprising a first end 831 attached to the inner body 10 and a second end 832 attached to the control portion 41 of the locking ring 40. The first end 831 is therefore attached axially and in rotation, while the second end 832 is attached axially but can move in rotation with the locking ring 40. The flexible element 83 passes into said recess 821 of the motor wheel 82, such that a movement of the latter will elastically deform said flexible element in one or the other direction and thus exert a lateral force on the locking ring 40 at said control part 410, thus forcing said locking ring 40 to rotate in one or the other direction.

The electronic board 90 comprises appropriate electronic elements, such as, in particular a microprocessor, for operating the device, in particular the motor 81 and the display 21.

Advantageously, the electronic board 90 also comprises a first switch 91 for detecting movement of the slider 70, and two second switches 92, 93 for detecting the angular position of the motor wheel 82. The first switch 91 makes it possible to detect the start of actuation. Thus, if after a predetermined time following the unlocking of the device, the user does not actuate the device, the latter may automatically return to the locking position. The first and second switches 91, 92, 93 make it possible to detect and record the actuation of the device; this information may be used for blocking the device for a predetermined time. Thus, the electronic board 90 may comprise time-out means to allow a new actuation only after the end of predetermined time-out. These time-out means may in particular comprise the inner clock of the microprocessor. Optionally, it is possible to adjoin a clock component to it in real time. This temporary blocking period preferably acts on the motor control unit 81, thus preventing the latter from rotating to move the locking ring 40 from the locking position to the releasing position. In a variant, the control button may be deactivated or blocked for a predetermined period of time. Advantageously, only authorised persons, such as medical personnel, may modify said blocking time by having access to the electronic board or via the display 21. Preferably, the electronic board 90 is arranged inside a side wall of the outer body 20, and the display 21 is arranged outside this same side wall.

Advantageously, the display 21 indicates how much time remains before the next dose can and/or must be loaded. Optionally, an audible and/or visual signal may also be provided if the user nevertheless presses the control button to attempt to unlock the device.

The operation of the device shown in the drawings will now be described in more detail.

Figures 18, 19:
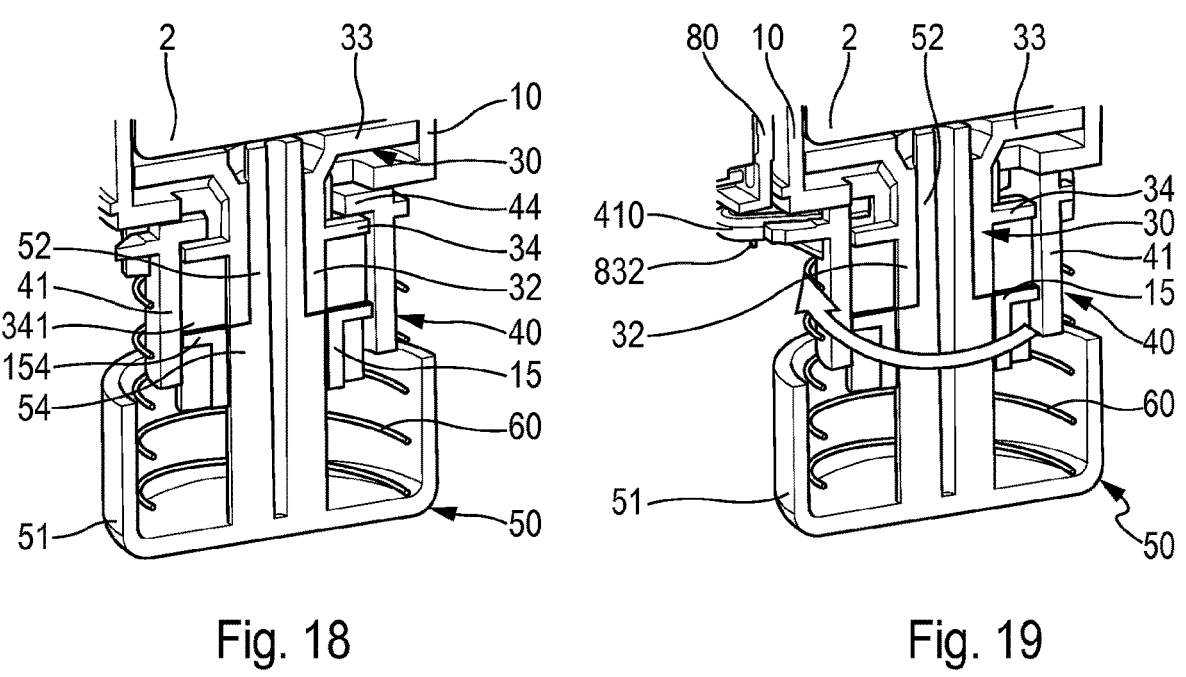
FIG. 18 is a cut-away diagrammatic and fragmentary perspective side view of the device before actuation, showing the locking ring in the locking position and the thrust and control members in the rest position.
FIG. 19 is a view similar to the view in FIG. 18, the locking ring being in the locking position.

In a normal actuation cycle, the user manually sets the device to the rest position, as shown in FIG. 18. In this position, it cannot move the actuator 50 axially upwards, because the latter is blocked by the locking ring 40 which is in the locking position.

Figures 26, 27, 28:
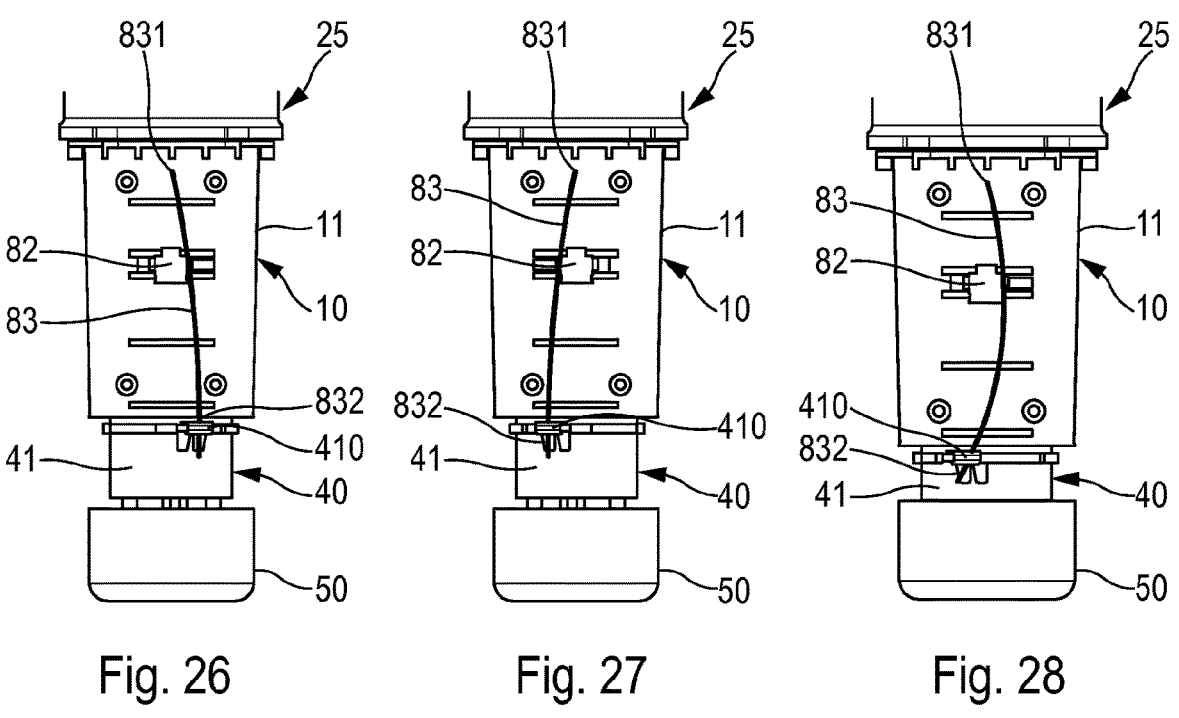
FIG. 26 is a diagrammatic and fragmentary perspective view showing the locking ring in the locking position, when forced by the flexible element.
FIG. 27 is a view similar to the view in FIG. 26, showing the locking ring in the releasing position, when forced by the flexible element.
FIG. 28 is a view similar to the view in FIG. 27, showing the flexible element forcing the locking ring towards the locking position, but with the locking ring blocked in the releasing position during actuation of the device.

To actuate the device, the user must first command the control module to move the locking ring 40 from the locking position to the releasing position. To do this, the user must press on a control button, which can advantageously be integrated into the display 21. This pressure will cause the motor 81 and therefore the motor wheel 82 to rotate in an actuating direction, which deform the flexible element 83 in a first direction, and thus force the locking ring 40 to rotate from the locking position, as can be seen in FIGS. 15, 18 and 26, to the releasing position, as can be seen in FIGS. 16, 19 and 27.

The user can then exert an axial actuating force on the control member 50 to move it axially upwards along the arrow F1, which will move the thrust member 30 and therefore the tank 2 concomitantly along the arrow F2, as can be seen in FIG. 20. This actuates the dispensing member 6 and expels a dose of fluid through the dispensing port 4, as can be seen in FIG. 16. Simultaneously, the upward axial movement of the thrust member 30 causes the same axial movement for the slider 70 attached to said thrust member 30. In the rest position, the portion of the projecting contact surface 72 of the slider does not contact the first switch or commutator 91. As soon as the slider 70 begins to move axially upwards, the projecting contact part 72 comes into contact with the first switch or commutator 91, as can be seen in FIG. 36, which sends a command to the motor 81. The latter then rotates in the direction opposite to the actuating direction, as does the motor wheel 82, thus causing the flexible element 83 to be deformed in a second direction, opposite to the first direction. The flexible element 83 therefore is deformed, as can be seen in FIG. 28, by forcing the locking ring 40 to the locking position. However, since the locking ring 40 is blocked in the releasing position from the start of the axial movement of the thrust member 30, it cannot return to the locking position under the effect of the force exerted by the flexible element 83 which has been deformed. The flexible element 83 is thus under stress throughout the entire actuation cycle.

When the user releases the axial actuating force, the spring 60 returns the thrust member 30 and the control member 50 to the rest position along the arrow F3, as can be seen in FIG. 21. In this rest position, the locking ring 40 is no longer blocked in rotation by the thrust member 30, as can be seen in FIG. 32, and it therefore returns automatically to the locking position under the effect of the stress exerted by the deformed flexible element 83, as can be seen in FIGS. 17, 21 and 33.

The device is then returned to the rest position, and a further actuation will only be possible after the end of the predetermined blocking period.

The device advantageously comprises various safety means for enabling and/or blocking the actuation of the device under certain particular conditions.

Thus, if the user presses strongly on the actuator 50 before actuating the control button, they can potentially block the rotation of the locking ring 40 to the releasing position, by friction of the radial extension 34 on the first flat inner surface 44. The device is advantageous because, when the control button is actuated, the motor 81 deforms the flexible element 83, and thus the locking ring 40 will turn to the releasing position as soon as the user relaxes his pressure on the actuator 50.

Moreover, as already mentioned above, it is possible to re-lock the device by returning the locking ring 40 to the locking position if the user has left the device unlocked for too long, for example if they have forgotten to take the dose.

Although the present invention is described above with reference to an advantageous embodiment, naturally various modifications can be applied thereto by the person skilled in the art, without going beyond the scope of the present invention, as defined by the accompanying claims.

The invention claimed is:

1. A device for dispensing a fluid product comprising:
said fluid product dispenser (1) having a tank (2) containing a fluid product, a dispensing head (3) having a dispensing port (4), said dispensing head (3) being axially movable with respect to said tank (2), and a dispensing member (6) mounted on said tank (2), said dispensing member (6) being actuated when said tank (2) is moved axially upwards with respect to said dispensing head (3);

an inner body (10) comprising a hollow cylinder (11) receiving said fluid product dispenser (1) and an axial extension (15) extending axially downwards from said hollow cylinder (11);

a control module (80, 81, 82, 83, 90) attached to said inner body (10), said control module comprising an electronic board (90), a motor (81) and a motor wheel (82) caused to rotate by said motor (81);

an outer body (20) receiving said inner body (10) and said control module;

a thrust member (30) in contact with said tank (2) and mounted so as to be axially movable on said inner body (10) between a rest position and an actuation position;

a control member (50) attached to said thrust member (30) and axially moving together therewith;

a locking ring (40) mounted on said axial extension (15) of said inner body (10) so as to be capable of rotating between locking and releasing positions, said locking ring (40) being moved between said locking and releasing positions by said control module, said locking ring (40) co-operating in the locking position with said thrust member (30) so as to prevent axial movement of said thrust member and co-operating in the releasing position with said thrust member (30) so as to enable axial movement of said thrust member towards the actuation position thereof.

2. The device according to claim 1, wherein said control module comprises a flexible element (83) attached on one side to said inner body (10) and on the other side to said locking ring (40), said motor wheel (82) co-operating with said flexible element (83) to deform said flexible element and thus move said locking ring (40) between the locking and releasing positions.

3. The device according to claim 2, wherein said flexible element (83) is a wire, or a flexible blade.

4. The device according to claim 2, wherein said control module is configured to deform said flexible element (83) from a start of the axial movement of the control member (50), so as to force said locking ring (40) to the locking position.

5. The device according to claim 1, wherein said axial extension (15) of said inner body (10) comprises a hollow axial cylinder (150) provided with at least one axial slot (151) extending over a portion of a height of said hollow axial cylinder, said hollow axial cylinder (150) comprising at least one radial wall (155) extending radially outwards entirely over the height of said hollow axial cylinder (150), said at least one radial wall (155) being angularly offset from each axial slot by 90°.

6. The device according to claim 5, wherein said hollow axial cylinder (150) comprises walls (155) two diametrically opposed axial slots of said at least one axial slot and two diametrically opposed radial walls of said at least one radial wall.

7. The device according to claim 5, wherein said thrust member (30) comprises an axial well (32) extending axially downwards from an upper plate (33) co-operating with said tank (2), said axial well (32) comprising at least one radial extension (34) extending radially outwards from the outer surface of said axial well (32), the upper axial surface (340) of each radial extension (34) being arranged away from said upper plate (33), each radial extension (34) being arranged in a respective axial slot (151) of said inner body (10).

8. The device according to claim 7, wherein said thrust member (30) comprises two radial extensions of said at least one radial extension (34) which are diametrically opposed.

9. The device according to claim 7, wherein said upper plate (33) of said thrust member (30) comprises, at an outer edge, a radial projection (31) for attaching a slider (70) co-operating during actuation with said control module.

10. The device according to claim 7, wherein said locking ring (40) comprises a hollow sleeve (41) provided with at least one first flat inner surface (44) extending radially inwards from an upper axial edge (411) of said hollow sleeve (41), each first flat inner surface (44) extending over a small part of an inner periphery of said hollow sleeve (41), said upper axial surface (340) of a respective radial extension of said at least one radial extension (34) of said thrust member (30) being in axial abutment against a respective first flat inner surface (44) when the locking ring (40) is in the locking position.

11. The device according to claim 10, wherein, in the releasing position of said locking ring (40), said at least one first flat inner surface (44) is angularly offset from said respective radial extension (34), thus allowing axial movement of said thrust member (30) relative to said inner body (10).

12. The device according to claim 7, wherein said at least one radial wall (155) is configured to co-operate with said locking ring (40) to define the locking and releasing positions.

13. The device according to claim 1, wherein said locking ring (40) is configured to be blocked in the releasing position throughout an actuation cycle, and to return automatically to the locking position at an end of said actuation cycle.

14. The device according to claim 1, wherein said control module comprises time-out means to prevent, after each actuation of the dispenser (1), movement of said locking ring (40) from the locking position to the releasing position for a predetermined period of time.

15. The device according to claim 14, wherein said time-out means are configured to block a control button of the device and/or said motor (81).

16. The device according to claim 1, in which said fluid product is a pharmaceutical product.

17. The device according to claim 16, wherein said pharmaceutical product is a drug.

18. The device according to claim 1, wherein said dispensing member is a pump or a valve.

* * * * *